United States Patent
Brandreth, III

(10) Patent No.: US 8,728,405 B2
(45) Date of Patent: May 20, 2014

(54) CHEMICAL DISPENSER ASSEMBLY

(76) Inventor: John B. Brandreth, III, Canton, GA (US)

( * ) Notice: Subject to any disclaimer, the term of this patent is extended or adjusted under 35 U.S.C. 154(b) by 149 days.

(21) Appl. No.: 13/286,761

(22) Filed: Nov. 1, 2011

(65) Prior Publication Data

US 2013/0108520 A1  May 2, 2013

(51) Int. Cl.
| | |
|---|---|
| B01D 11/02 | (2006.01) |
| B01D 35/00 | (2006.01) |
| E03B 11/00 | (2006.01) |
| A01N 25/12 | (2006.01) |
| A61L 2/00 | (2006.01) |
| B01F 1/00 | (2006.01) |
| B67D 3/00 | (2006.01) |
| B67D 7/76 | (2010.01) |
| C02F 1/10 | (2006.01) |
| C02F 11/14 | (2006.01) |
| C12H 1/044 | (2006.01) |

(52) U.S. Cl.
CPC . *A01N 25/12* (2013.01); *A61L 2/00* (2013.01); *B01F 1/00* (2013.01); *B67D 3/0032* (2013.01); *B67D 7/76* (2013.01); *C02F 1/10* (2013.01); *C02F 2201/00* (2013.01); *C02F 11/14* (2013.01); *C12H 1/0408* (2013.01)
USPC ........... 422/261; 422/255; 422/265; 210/206; 137/268

(58) Field of Classification Search
CPC ............ A01N 25/12; A61L 2/00; B01F 1/00; B67D 3/0032; B67D 7/76; C02F 1/10; C02F 2201/00; C02F 11/14; C12H 1/0408
USPC ........... 422/255, 261, 265; 210/206; 137/268, 137/551
See application file for complete search history.

(56) References Cited

U.S. PATENT DOCUMENTS

| | | | |
|---|---|---|---|
| 2,135,932 A | 11/1938 | Belmont | |
| 2,869,926 A | 1/1959 | Lundquist | |
| 2,885,271 A | 5/1959 | Kersh | |
| 2,955,923 A | 10/1960 | Atkinson | |
| 3,306,709 A | 2/1967 | Atkinson | |
| 3,442,800 A | 5/1969 | Jasionowski | |
| 3,447,753 A | 6/1969 | Proctor et al. | |
| 3,887,468 A | 6/1975 | Bray | |
| 4,059,522 A | 11/1977 | Polley et al. | |
| 4,347,224 A | 8/1982 | Beckert et al. | |
| 4,780,197 A | 10/1988 | Schuman | |
| 5,053,206 A | 10/1991 | Maglio et al. | |
| 5,181,533 A | 1/1993 | Kooi | |
| 5,507,945 A | 4/1996 | Hansen | |
| 5,580,448 A * | 12/1996 | Brandreth, III | ............... 210/206 |
| 6,267,886 B1 | 7/2001 | Brandreth, III | |
| 6,274,038 B1 * | 8/2001 | Reid | ............... 210/206 |
| 6,280,617 B1 | 8/2001 | Brandreth, III | |
| 6,855,252 B2 | 2/2005 | Brandreth, III | |

* cited by examiner

*Primary Examiner* — Monzer R Chorbaji
(74) *Attorney, Agent, or Firm* — Thomas C. Saitta

(57) ABSTRACT

A chemical dispensing assembly having a base member, a flow chamber, a chemical chamber and a dispensing control conduit, wherein water or other liquid flows through the base member, into the flow chamber, through the dispensing control conduit and out the base member, wherein a small amount of saturated solution retained within the chemical chamber is drawn into the water flow, the chemical chamber being connected below the flow chamber and the volume of the chemical chamber being greater than the volume of the flow chamber. Preferably, the flow chamber is connected to the base member with a bayonet-type connection mechanism, and keys and key slots are provided such that only dedicated flow chambers can be connected to the base member.

19 Claims, 3 Drawing Sheets

CHEMICAL DISPENSER ASSEMBLY

BACKGROUND OF THE INVENTION

This invention relates generally to the field of dispenser devices used to introduce small quantities of a chemical solution into a flowing liquid, the chemical solution being created by dissolving a solid or granular chemical. More particularly, the invention relates to such devices to be used as a component in assemblies of the type commonly found in liquid circulation or supply systems, such as water supply systems, where the rate of introduction of the dissolved chemical into the water is proportional to the flow volume of the water stream to insure proper concentration percentage.

It is desirable or necessary in many water supply or recirculation systems, such as water for household or industrial use, or water for use in spas and pools, to add certain chemicals to the water to control bacteria or fungal growth, corrosion, scale deposits, etc. Commonly known additives include chlorine, polyphosphate or sodium silicate. Such additives are typically supplied in solid or granular form for ease of handling, and must therefore be dissolved in liquid and introduced into the water flow. It is imperative that the chemical additives be supplied in the proper concentration, and it is important that the mechanism for adding the chemical solutions provide for proper rate introduction with little variation in concentration. Many conventional systems fail these criteria, the mechanisms being unable to prevent variations in concentration and introduction rates, especially in circumstances where the water flow is not continuous and varies in pressure The most simplistic solid chemical additive mechanisms simply divert all or a portion of the water flow stream through a container holding the solid chemical. The water flowing from the container will then include an amount of dissolved chemical. These devices suffer from lack of dispensing control, since the amount of chemical present in the outflow is dependent on the volume of solid chemical in the container. As that volume decreases, the concentration of dissolved chemical in the outflow also decreases. Additionally, this type of system produces a highly concentrated chemical surge when water flow is resumed after being shut off for a period of time, since the lack of flow allows the chemical solution to become saturated. Finally, variation in the water flow rate will not correspondingly alter the dissolving rate of the chemical, producing incorrect concentration amounts in the outflow.

Attempts have been made to develop a mechanism which addresses the problems encountered in correctly metering and controlling the chemical introduction and concentration rates, but known systems are either overly complicated or do not fully solve all the problems set forth above. A complicated mechanism is described in U.S. Pat. No. 4,780,197 to Schuman, which discloses a flow-through chemical dispenser cartridge positioned within the internal core of a filter which requires one or more operational valves to perform effectively. A more simplified approach is shown in U.S. Pat. No. 4,347,224 to Beckert et al. This patent discloses a flow housing which contains an internally mounted chemical cartridge. A small amount of the water flow is diverted into the bottom of the chemical cartridge and the chemical solution is drawn through a small aperture in the top of the cartridge by the pressure differential created by the flow of the bulk of the water passing through the housing. This apparatus provides a simple approach to solving the problems encountered in standard solid chemical systems, but the mechanism is just a variation of the standard system where a portion of the water stream is passed through the solid chemical before being returned to the main flow stream. The distinction in Beckert et al. is that the cartridge containing the solid chemical is mounted internal to a large housing through which all the water flows. The sizing of the cartridge is such to create an annular passage down to the bottom of the chemical cartridge, where the water flows through a plurality of liquid inlet holes, past the chemical and out the liquid outlet hole. In effect, the annular passage is just a substitute for a small bypass conduit as found in many old systems, and the problems associated with variations in concentration and surging would still be present.

These problems have been addressed in various embodiments in my previous U.S. Pat. Nos. 5,580,448, 6,267,886, 6,280,617 and 6,855,252, the disclosures of which are incorporated herein by reference. However, a drawback inherent in these patents is that the chemical dispenser units are designed to be retained within the standard housings, bowls or bells used in combination with the standard inline base members. As such, the chemical dispenser units are limited in size, and replacement of the units once the chemical has been depleted requires multiple steps.

It is an object of this invention to provide a chemical dispenser device or assembly which provides a steady state concentration of dissolved chemical, which introduces the chemical solution into the main water stream in amounts directed related to water flow rate or volume to maintain precise percentages of chemical solution, which does not produce excessive chemical concentration during periods of no water flow, and which does not introduce excessive amounts of dissolved chemical when water flow is resumed, and wherein the chemical dispenser device is structured such that the amount of the solid chemical is not limited by the size of the standard housing, and further wherein removal and replacement of the chemical dispenser unit is quickly and easily accomplished, and further wherein in certain embodiments the volume of solid chemical and the dispensing rate can be changed by replacing certain components of the assembly, and further wherein in certain embodiments the connection mechanism for joining the chemical dispenser unit to the inline base member is a keyed, bayonet-type connection rather than a universal connection mechanism.

SUMMARY OF THE INVENTION

The invention is a chemical dispensing assembly comprising a flow-through inline base member having an inlet opening connected to a water or other liquid supply conduit, an outlet opening connected to a water or other liquid outflow conduit, the base member structured to releasably receive a flow chamber with a dispensing control conduit. A downflow opening in the base member diverts water from the inlet opening into the flow chamber and through the dispensing control conduit, and a centrally located upflow opening in the base member receives water from the dispensing control conduit and directs it through the outflow opening and into the outflow conduit. The dispensing control conduit comprises a tubular body having an outflow opening and a plurality of inflow apertures to accommodate large volume water flow, a transverse wall positioned below the inflow apertures and having a relatively small dispensing aperture, and at least one relatively small intake aperture positioned below the transverse wall. The flow chamber comprises a central opening that communicates with a chemical chamber attached to the bottom of the flow chamber, the chemical chamber retaining a quantity of chemical or other solid substances to be dissolved and dispensed into the water flow, whereby the flow chamber is an upper chamber and the chemical chamber is a lower chamber, and further whereby the lower chemical chamber has a larger internal diameter than the internal diameter of the dispensing control conduit.

The connection mechanism for releasably joining the flow chamber to the base member may comprise a standard threaded mechanism, in preferred embodiments the flow chamber is temporarily mounted to the base member using a bayonet-type mechanism. The connection mechanism may further comprise key members whereby the flow chamber must be dedicated and matched to the particular base member in order to achieve mating. Furthermore, in other embodiments the chemical chamber may be releasably connected to the flow chamber such that the volume of the chemical chamber can be changed or the chemical refilled after depletion. In other embodiments, the dispensing control conduit may be removable such that it may be replaced by a control conduit having different sizes or numbers of the inflow apertures, dispensing aperture, or intake apertures.

When water flows through the assembly the pressure differential caused by the large volume flow of water through the inflow apertures of the dispensing control conduit and across the small dispensing aperture in the transverse wall draws a small amount of dissolved chemical solution through the dispensing aperture and into the main water flow stream, while simultaneously drawing an equally small amount of replacement water through the intake apertures and into the chemical chamber to replace the suctioned chemical solution. Because the intake apertures and the dispensing aperture are small in relation to the internal volume of the chemical chamber, the solution contained within the chemical chamber becomes chemically saturated within a short time after water is first introduced into the assembly. The solution within the chemical chamber remains saturated even when water flow is occurring, since the amount of water drawn into the intake apertures to replace the amount of chemical solution drawn out of the dispensing aperture is proportionately small relative to the total volume of the saturated solution contained within the chemical chamber. Because the solution in the chemical chamber is constantly in a saturated state, there will be no change in concentration during periods when no water flow is occurring.

In a first sense, an embodiment of the chemical dispenser assembly comprises: a base member comprising an inlet opening, an outlet opening, a downflow opening in communication with said inlet opening, and a central upflow opening in communication with said outlet opening; a flow chamber connected to said base member, said flow chamber comprising a side wall, a bottom, and a central opening in said bottom; a chemical chamber connected to said flow chamber, said chemical chamber positioned below said flow chamber, said chemical chamber comprising a side wall and a bottom; and a dispensing control conduit extending between said central upflow opening of said base member and said central opening of said flow chamber, said dispensing control conduit comprising a tubular body, an outflow opening, inflow apertures disposed in said tubular body, a transverse wall positioned below said inflow apertures, a dispensing aperture disposed in said transverse wall, and an intake aperture disposed in said tubular body below said transverse wall; whereby water entering said base member inlet opening passes through said base member downflow opening into said flow chamber, through said dispensing control conduit intake apertures, through said dispensing control conduit outflow opening, through said base member upflow opening and through said base member outlet opening, and further whereby a small amount of said water passes through said dispensing control conduit intake aperture into said chemical chamber, and further whereby a small amount of water passes from said chemical chamber through said dispenser control conduit dispensing aperture.

In a second sense, an embodiment of the chemical dispensing assembly is a water supply system chemical dispenser assembly comprising: a base member comprising an inlet opening, an outlet opening, a downflow opening in communication with said inlet opening, and a central upflow opening in communication with said outlet opening, said inlet opening connectable to an inflow conduit of a water supply system, said outlet opening connectable to an outlet conduit of a water supply system; a flow chamber removably connected to said base member, said flow chamber comprising a side wall, a bottom, and a central opening in said bottom; a chemical chamber connected to said flow chamber, said chemical chamber positioned below said bottom of said flow chamber, said chemical chamber comprising a side wall and a bottom, the interior volume of said chemical chamber being greater than the interior volume of said flow chamber; and a dispensing control conduit extending between said central upflow opening of said base member and said central opening of said flow chamber, said dispensing control conduit comprising a tubular body, an outflow opening, inflow apertures disposed in said tubular body, a transverse wall positioned below said inflow apertures, a dispensing aperture disposed in said transverse wall, and an intake aperture disposed in said tubular body below said transverse wall, wherein the interior diameter of said tubular body and said flow chamber central opening is smaller than the interior diameter of said chemical chamber; a soluble chemical disposed in said chemical chamber; whereby water entering said base member inlet opening passes through said base member downflow opening into said flow chamber, through said dispensing control conduit intake apertures into said dispensing control conduit, through said dispensing control conduit outflow opening, through said base member upflow opening and through said base member outlet opening, and further whereby a small amount of said water passes through said dispensing control conduit intake aperture into said chemical chamber, thereby dissolving said chemical and creating a saturated chemical solution, and further whereby a small amount of saturated chemical solution passes from said chemical chamber through said dispenser control conduit dispensing aperture and into said dispensing control conduit.

In a third sense, an embodiment of the chemical dispensing assembly is a water supply system chemical dispenser assembly comprising: a base member comprising an inlet opening, an outlet opening, a downflow opening in communication with said inlet opening, and a central upflow opening in communication with said outlet opening, said inlet opening connectable to an inflow conduit of a water supply system, said outlet opening connectable to an outlet conduit of a water supply system; a flow chamber removably connected to said base member, said flow chamber comprising a side wall, a bottom, and a central opening in said bottom; a chemical chamber connected to said flow chamber, said chemical chamber positioned below said bottom of said flow chamber, said chemical chamber comprising a side wall and a bottom, the interior volume of said chemical chamber being greater than the interior volume of said flow chamber; and a dispensing control conduit extending between said central upflow opening of said base member and said central opening of said flow chamber, said dispensing control conduit comprising a tubular body, an outflow opening, inflow apertures disposed in said tubular body, a transverse wall positioned below said inflow apertures, a dispensing aperture disposed in said transverse wall, and an intake aperture disposed in said tubular body below said transverse wall, wherein the interior diameter of said tubular body and said flow chamber central opening is smaller than the interior diameter of said chemical chamber; a soluble chemical disposed in said chemical chamber; wherein said flow chamber is connected to said base member by a bayonet-type connection mechanism, said connection mechanism comprising outwardly extending wedging flanges disposed on said flow chamber and inwardly extending wedging flanges disposed on said base member, said wedging flanges having abutting inclined surfaces, and wedge-receiving slots sized to allow passage of said wedging flanges disposed on said flow chamber and said base member, whereby said flow chamber is connected to said base member by inserting said flow wedging flanges through said wedge-receiving slots and rotating said flow chamber; and whereby water entering said base member inlet opening passes through said base member downflow opening into said flow chamber, through said dispensing control conduit intake apertures into said dispensing control conduit, through said dispensing control conduit outflow opening, through said base member upflow opening and through said base member outlet opening, and further whereby a small amount of said water passes through said dispensing control conduit intake aperture into said chemical chamber, thereby dissolving said chemical and creating a saturated chemical solution, and further whereby a small amount of saturated chemical solution passes from said chemical chamber through said dispenser control conduit dispensing aperture and into said dispensing control conduit.

Furthermore, the embodiments of the chemical dispensing assembly may also comprise key slots and corresponding keys, whereby said keys pass through said key slots when said wedging flanges are inserted through said wedge-receiving slots.

DETAILED DESCRIPTION OF THE INVENTION

Figure 1:
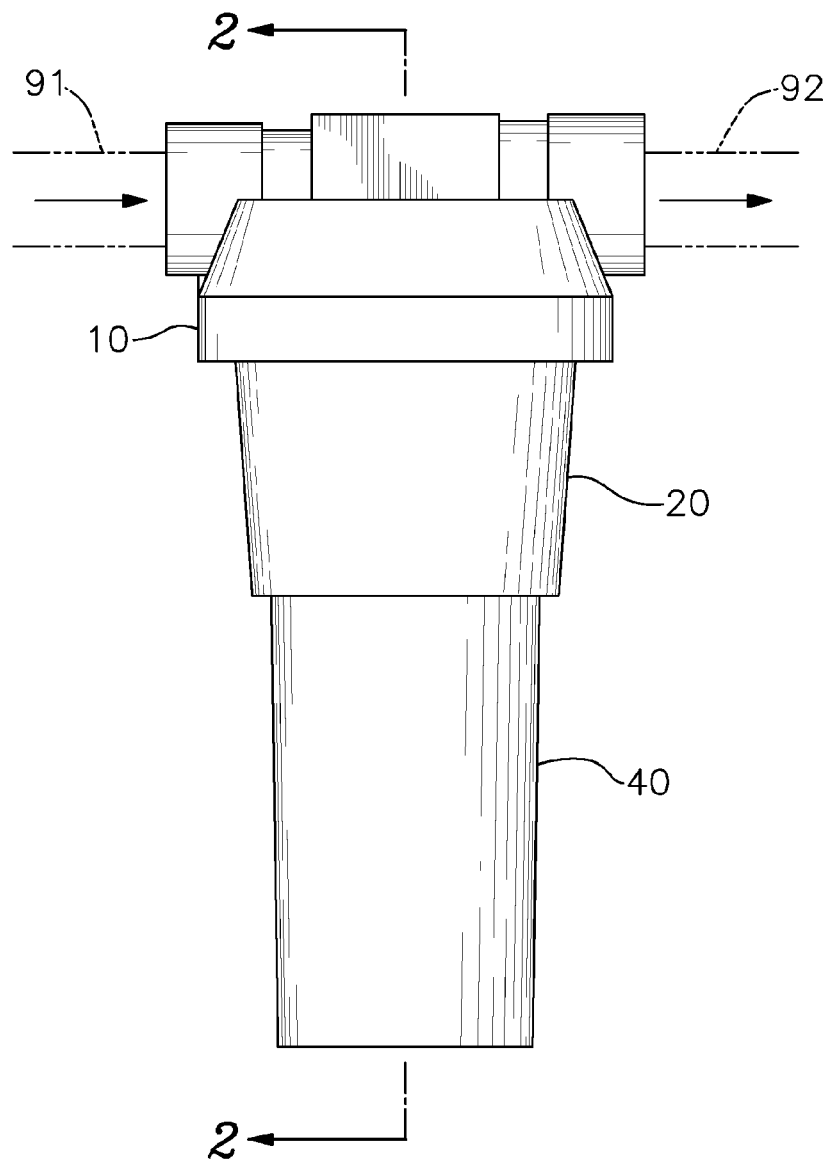
FIG. 1 illustrates an embodiment of the chemical dispenser assembly showing the base member, upper flow chamber and lower chemical chamber.

With reference to the drawings, the various embodiments of the invention will be described in detail with regard for the best mode and the preferred embodiment or embodiments. In general, the invention is a chemical dispenser device or assembly for the purpose of introducing a chemical solution into a flow of liquid, such as for example introduction of chlorine, polyphosphate or other chemicals into water supply systems to control bacterial or fungal growth, corrosion, scale deposits, etc. The assembly is preferably composed of plastic materials, although other materials of construction are possible. In the following disclosure, the term "water" shall be used as a general term of convenience to inclusively represent any liquid to be passed through the assembly.

The chemical dispensing assembly comprises a flow-through inline base member 10 having an inlet opening 11 connected to a water supply conduit or pipe 91, an outlet opening 12 connected to a water outflow conduit or pipe 92, the base member 10 structured to releasably receive a flow chamber 20 with a dispensing control conduit 30. A downflow opening 13 in the base member 10 diverts water from the inlet opening 11 into the flow chamber 20 and through the dispensing control conduit 30, and a centrally located upflow opening 14 in the base member 10 receives water from the dispensing control conduit 30 and directs it through the outflow opening 12 and into the outflow conduit 92. Such base members 10 are well known in the industry. One distinguishing characteristic of the base member 10 of the invention is that most preferably the inlet opening 11, the downflow opening 13, the upflow opening 14, the outlet opening 12, and the connecting passages therefore are sized sufficiently such that the flow rate of the water passing through the base member 10 is not impeded or diminished.

Figure 7:
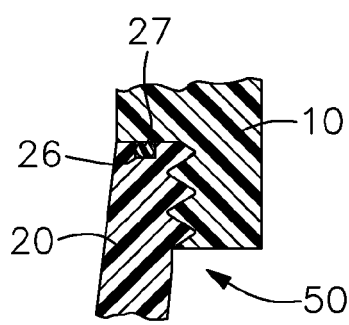
FIG. 7 is a partial view showing an alternate embodiment of a releasable flow chamber connection mechanism joining the flow chamber to the base member.

The flow chamber 20 comprises a side wall 21 and a bottom 22. A central opening 23 is positioned in the flow chamber bottom 22 that communicates with a chemical chamber 40 which is attached to the bottom 22 of the flow chamber 20, the chemical chamber 40 retaining a quantity of a soluble chemical, mixture or other substance 99, in solid, granular, or powder form for example, to be dissolved and dispensed into the water flow. The flow chamber connection mechanism 50 for releasably joining the flow chamber 20 to the base member 10 may comprise a standard combination of mating threaded structural elements comprising outwardly extending external threading 58 on the flow chamber 20 and inwardly extending internal threading 57 on the base member 10, whereby the flow chamber 20 can be screwed onto or from the base member 10, as shown in FIG. 7.

In preferred embodiments the flow chamber 20 is temporarily mounted to the base member using a bayonet-type connection mechanism 50 whereby the underside of the base member 10 is provided with wedge-receiving slots 53 and inwardly extending wedging flanges 54 each having an inclined upper surface, and whereby the top of the flow chamber 20 is provided with corresponding wedge-receiving slots 53 and outwardly extending wedging flanges 55 each having an inclined lower surface. With this flow chamber connection mechanism 50 the flow chamber 40 is aligned so that the wedging flanges 54 and 55 pass through the wedge-receiving slots 53 and the flow chamber 20 is turned. In known manner the abutting of the inclined surfaces of the base member wedging flanges 54 and the flow chamber wedging flanges 55 in combination cause the flow chamber 20 to be securely pressed against the base member 10 in fluid-tight manner. Preferably, the top of the flow chamber 20 is provided with an O-ring channel 26 and an O-ring 27 to better seal the connection. In the embodiments shown the flow chamber 20 fits internally within the base member 10, but the elements could be reversed whereby the flow chamber 20 fits externally onto the base member 10.

Figure 4:
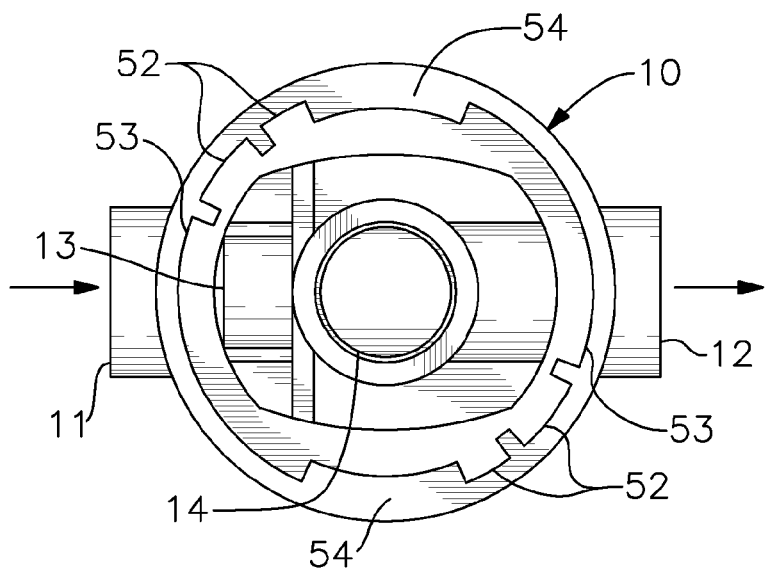
FIG. 4 is a view of an embodiment of the interior of the inline base member, showing components of the keyed, bayonet-type connection mechanism.
Figure 5:
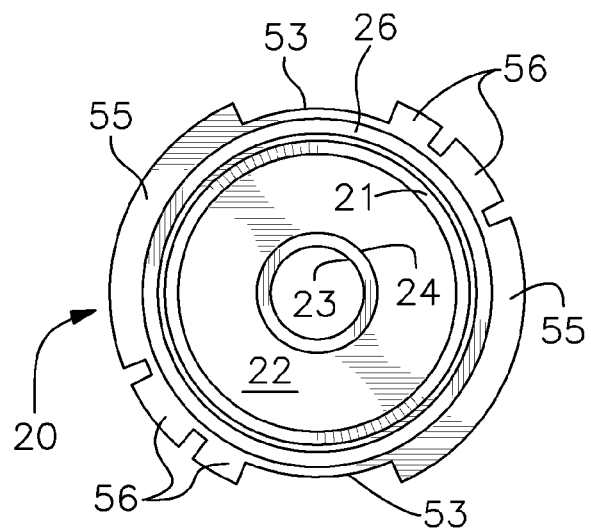
FIG. 5 is a view of an embodiment of the removable flow chamber corresponding to the embodiment of the inline base member of FIG. 4.

As best shown in FIGS. 4 and 5, the flow chamber connection mechanism 50 may further comprise key members 56 disposed on the flow chamber 20, the key members 56 corresponding in location to key slots 52, whereby the flow chamber 20 must be matched to a particular base member 10 in order to achieve mating. Properly located and sized key members 56 will fit into the key slots 52 when the flow chamber 20 is first brought in contact with the base member 10, thereby allowing the flow chamber 20 to be turned relative to the base member 10. A different flow chamber 20 having key members 56 that are differently sized and/or spaced will not be able to be mated since the key members 56 will not pass into the key slots 52. Alternatively, the key members 56 may be disposed on the base member 10 with the corresponding key slots 52 disposed on the flow chamber 20.

Figure 6:
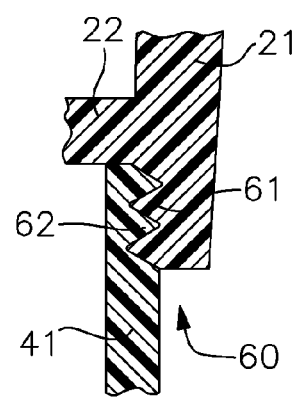
FIG. 6 is a partial view showing an embodiment of a releasable chemical chamber connection mechanism joining the chemical chamber to the flow chamber.

A chemical chamber 40 comprising a side wall 41 and bottom 42 is formed with or connected to the bottom 22 of the flow chamber 20, preferably within a recess 25 as shown. The chemical chamber 40 is open at the top and retains a quantity of solid chemical 99 in block, granular or powder form, the chemical 99 being soluble in water. The chemical chamber 40 may be permanently attached to the flow chamber 20, or may be releasably attached using a chemical chamber connection mechanism 60. For example, the chemical chamber connection mechanism 60 may comprise mating threads, such as internal threading 61 disposed on the flow chamber 20 and external threading 62 disposed on the chemical chamber 40, as shown in FIG. 6. By providing a removable chemical chamber 40, the chemical chamber 40 can be refilled with solid chemical 99 when the original is depleted, different chemicals 99 can be substituted, or the chemical chamber 40 can be replaced with different size chemical chambers 40, for example. Furthermore, the chemical chamber connection mechanism 60 may be reversed such that the chemical chamber 40 mounts onto the exterior of the side wall 21 of the flow chamber 20.

Figure 3:
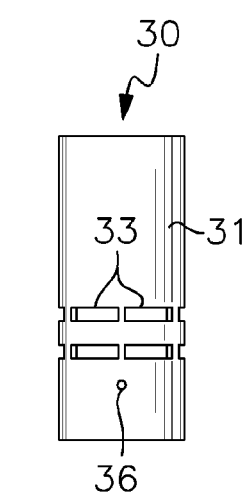
FIG. 3 illustrates an embodiment of the dispensing control conduit as removed from the chemical dispenser assembly.
Figure 2:
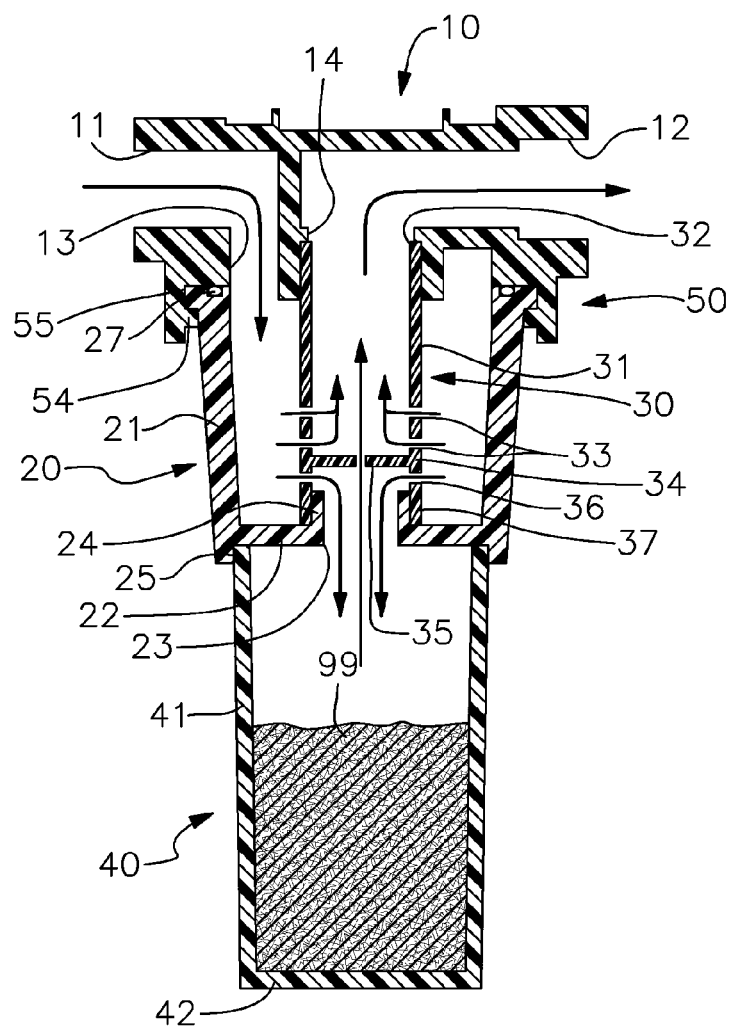
FIG. 2 is a cross-sectional view taken along line 2-2 of the chemical dispenser assembly shown in FIG. 1, showing the base member, upper flow chamber, lower chemical chamber and the dispensing control conduit.

The dispensing control conduit 30, as shown in FIGS. 2 and 3, comprises a tubular body 31 having an upper outflow opening 32, a plurality of inflow apertures 33 on the tubular body 31 sized and numbered to accommodate large volume water flow without reducing or impeding the flow rate through the system, i.e., the total area of all the inflow apertures 33 is equal to or greater than the area of the base member downflow opening 13, a transverse wall 34 positioned below the inflow apertures 33 and extending across the interior of the tubular body 31, a relatively small dispensing aperture 35 positioned in the transverse wall 34, and at least one relatively small intake aperture 36 positioned on the tubular body 31 below the transverse wall 34. The lower portion of the tubular body may define an annular mounting sleeve 37, the annular mounting sleeve 37 corresponding in size to an annular mounting flange 24 surrounding the opening 23 of the flow chamber 20, such that the dispensing control conduit 30 may be connected to the flow chamber with a friction fit. The annular mating sleeve 37 may be sized to snugly receive the annular mounting flange 24, as shown in FIG. 2, or the dimensions may be reversed such that the annular mating sleeve 37 is received within the annular mounting flange 24. Alternative connection mechanisms may be employed, such as by threaded connections for example, or the dispensing control conduit 30 may be permanently affixed to the flow chamber 20. Providing a removable dispensing control conduit 30 allows for replacement with a control conduit 30 having different sizes or numbers of the inflow apertures 33, dispensing aperture 35, or intake apertures 36 to account for or provide different water flow rates. The upper end of the tubular body 31 is received within the central upflow opening 14 of the base member 10 such that all water within the flow chamber 20 must pass through the dispensing control conduit 30 before exiting the base member 10.

Thus, the chemical dispensing assembly comprises a flow chamber 20 that is an upper chamber and a chemical chamber 40 that is a lower chamber. The open interior volume of the upper flow chamber 20 is sized such that flow from the inflow conduit 92 is not reduced or impeded after the water enters the flow chamber 20. The bottom 22 of the flow chamber 20 does not extend significantly beyond the lower end of the dispensing control conduit 30, and preferably does not extend any distance beyond the lower end of the dispensing control conduit 30, as no purpose is served by water flow any significant distance below the intake apertures 36. The open interior volume of the chemical chamber 40 is sized such that the internal diameter of the chemical chamber is significantly greater than the internal diameter of the flow chamber central opening 23 and the internal diameter of the dispensing control conduit 30, thereby allowing a large amount of chemical 99 to be retained within the chemical chamber 40. Likewise, the interior volume of the lower chemical chamber 40 is greater than the interior volume of the upper flow chamber 20.

Initial filling of the chemical chamber 40 with water results in the formation of a saturated chemical solution within the area bounded by the chemical chamber 40 and the transverse wall 34. Water may be added directly into the chemical chamber 40 by removing the dispensing control conduit 30 prior to connecting the flow chamber 20 to the base member 10. Alternatively, the flow chamber 20 may be connected to the base member 10 and water flow initiated, whereby water will be drawn into the chemical chamber 40 through the intake apertures 36 due to the suction effect created on the dispensing aperture 35 by the large volume of water passing through the inflow apertures 33 of the dispensing control conduit.

When water flows through the assembly the pressure differential caused by the large volume flow of water through the inflow apertures 33 of the dispensing control conduit 30 and across the small dispensing aperture 35 in the transverse wall 34 draws a small amount of dissolved chemical solution through the dispensing aperture 35 and into the main water flow stream passing through the tubular body 31, while simultaneously drawing an equally small amount of water through the intake apertures 36 and into the chemical chamber 40 to replace the suctioned chemical solution, as shown in FIG. 2. Because the intake apertures 36 and the dispensing aperture 35 are small in relation to the internal volume of the chemical chamber 40, the solution contained within the chemical chamber 40 remains saturated even when water flow is occurring, since the amount of water drawn into the intake apertures 36 to replace the amount of chemical solution drawn out of the dispensing aperture 35 is proportionately small relative to the total volume of the saturated solution contained within the chemical chamber 40. Because the solution in the chemical chamber 40 is constantly in a saturated state, there will be no change in concentration during periods when no water flow is occurring.

With the embodiments as described above, the chemical dispensing assembly can be provided as either a refillable assembly or a disposable assembly. It is understood that equivalents and substitutions for certain elements set forth above may be obvious to those of ordinary skill in the art, and therefore the true scope and definition of the invention is to be as set forth in the following claims.

I claim:

1. A chemical dispenser assembly comprising:
   a base member comprising an inlet opening, an outlet opening, a downflow opening in communication with said inlet opening, and a central upflow opening in communication with said outlet opening;

a flow chamber connected to said base member, said flow chamber comprising a side wall, a bottom, and a central opening in said bottom, said flow chamber depending beneath said base member;

a chemical chamber connected to said flow chamber, said chemical chamber positioned below and externally to said flow chamber, said chemical chamber comprising a side wall and a bottom; and a dispensing control conduit extending between said central upflow opening of said base member and said central opening of said flow chamber, said dispensing control conduit comprising a tubular body, an outflow opening, inflow apertures disposed in said tubular body, a transverse wall positioned below said inflow apertures, a dispensing aperture disposed in said transverse wall, and an intake aperture disposed in said tubular body below said transverse wall;

whereby water entering said base member inlet opening passes through said base member downflow opening into said flow chamber, through said dispensing control conduit intake apertures, through said dispensing control conduit outflow opening, through said base member upflow opening and through said base member outlet opening, and further whereby a small amount of said water passes through said dispensing control conduit intake aperture into said chemical chamber, and further whereby a small amount of water passes from said chemical chamber through said dispenser control conduit dispensing aperture.

2. The assembly of claim 1, wherein said flow chamber is removably connected to said base member.

3. The assembly of claim 2, wherein said flow chamber is connected to said base member by a connection mechanism, said connection mechanism comprising threading disposed on said flow chamber and said base member.

4. The assembly of claim 2, wherein said flow chamber is connected to said base member by a connection mechanism, said connection mechanism comprising a bayonet-type connection.

5. The assembly of claim 4, said connection mechanism comprising wedging flanges disposed on said flow chamber and said base member, said wedging flanges having inclined surfaces.

6. The assembly of claim 5, said connection mechanism further comprising key slots and corresponding keys.

7. The assembly of claim 1, wherein said chemical chamber is removably connected to said flow chamber.

8. The assembly of claim 1, wherein said dispensing control conduit is removably connected to said flow chamber.

9. The assembly of claim 1, wherein the volume of said chemical chamber is greater than the volume of said flow chamber.

10. A water supply system chemical dispenser assembly comprising:

a base member comprising an inlet opening, an outlet opening, a downflow opening in communication with said inlet opening, and a central upflow opening in communication with said outlet opening, said inlet opening adapted to matingly receive an inflow conduit of a water supply system, said outlet opening adapted to matingly receive an outlet conduit of a water supply system;

a flow chamber removably connected to said base member, said flow chamber comprising a side wall, a bottom, and a central opening in said bottom, said flow chamber depending beneath said base member;

a chemical chamber connected to said flow chamber, said chemical chamber positioned below and externally to said bottom of said flow chamber, said chemical chamber comprising a side wall and a bottom, the interior volume of said chemical chamber being greater than the interior volume of said flow chamber; and a dispensing control conduit extending between said central upflow opening of said base member and said central opening of said flow chamber, said dispensing control conduit comprising a tubular body, an outflow opening, inflow apertures disposed in said tubular body, a transverse wall positioned below said inflow apertures, a dispensing aperture disposed in said transverse wall, and an intake aperture disposed in said tubular body below said transverse wall, wherein the interior diameter of said tubular body and said flow chamber central opening is smaller than the interior diameter of said chemical chamber;

a soluble chemical disposed in said chemical chamber;

whereby water entering said base member inlet opening passes through said base member downflow opening into said flow chamber, through said dispensing control conduit intake apertures into said dispensing control conduit, through said dispensing control conduit outflow opening, through said base member upflow opening and through said base member outlet opening, and further whereby a small amount of said water passes through said dispensing control conduit intake aperture into said chemical chamber, thereby dissolving said chemical and creating a saturated chemical solution, and further whereby a small amount of saturated chemical solution passes from said chemical chamber through said dispenser control conduit dispensing aperture and into said dispensing control conduit.

11. The assembly of claim 10, wherein said flow chamber is connected to said base member by a connection mechanism, said connection mechanism comprising a bayonet-type connection.

12. The assembly of claim 11, said connection mechanism comprising mating wedging flanges disposed on said flow chamber and said base member, said wedging flanges having abutting inclined surfaces, and wedge-receiving slots sized to allow passage of said wedging flanges;

whereby said flow chamber is connected to said base member by inserting said wedging flanges through said wedge-receiving slots and rotating said flow chamber.

13. The assembly of claim 12, said connection mechanism further comprising key slots and corresponding keys, whereby said keys pass through said key slots when said wedging flanges are inserted through said wedge-receiving slots.

14. The assembly of claim 10, wherein said chemical chamber is removably connected to said flow chamber.

15. The assembly of claim 10, wherein said dispensing control conduit is removably connected to said flow chamber.

16. A water supply system chemical dispenser assembly comprising:

a base member comprising an inlet opening, an outlet opening, a downflow opening in communication with said inlet opening, and a central upflow opening in communication with said outlet opening, said inlet opening adapted to matingly receive an inflow conduit of a water supply system, said outlet opening adapted to matingly receive an outlet conduit of a water supply system;

a flow chamber removably connected to said base member, said flow chamber comprising a side wall, a bottom, and a central opening in said bottom, said flow chamber depending beneath said base member;

a chemical chamber connected to said flow chamber, said chemical chamber positioned below and externally to said bottom of said flow chamber, said chemical chamber comprising a side wall and a bottom, the interior volume of said chemical chamber being greater than the interior volume of said flow chamber; and a dispensing control conduit extending between said central upflow opening of said base member and said central opening of said flow chamber, said dispensing control conduit comprising a tubular body, an outflow opening, inflow apertures disposed in said tubular body, a transverse wall positioned below said inflow apertures, a dispensing aperture disposed in said transverse wall, and an intake aperture disposed in said tubular body below said transverse wall, wherein the interior diameter of said tubular body and said flow chamber central opening is smaller than the interior diameter of said chemical chamber;

a soluble chemical disposed in said chemical chamber;

wherein said flow chamber is connected to said base member by a bayonet-type connection mechanism, said connection mechanism comprising outwardly extending wedging flanges disposed on said flow chamber and inwardly extending wedging flanges disposed on said base member, said wedging flanges having abutting inclined surfaces, and wedge-receiving slots sized to allow passage of said wedging flanges disposed on said flow chamber and said base member, whereby said flow chamber is connected to said base member by inserting said flow wedging flanges through said wedge-receiving slots and rotating said flow chamber; and whereby water entering said base member inlet opening passes through said base member downflow opening into said flow chamber, through said dispensing control conduit intake apertures into said dispensing control conduit, through said dispensing control conduit outflow opening, through said base member upflow opening and through said base member outlet opening, and further whereby a small amount of said water passes through said dispensing control conduit intake aperture into said chemical chamber, thereby dissolving said chemical and creating a saturated chemical solution, and further whereby a small amount of saturated chemical solution passes from said chemical chamber through said dispenser control conduit dispensing aperture and into said dispensing control conduit.

17. The assembly of claim 16, said connection mechanism further comprising key slots and corresponding keys, whereby said keys pass through said key slots when said wedging flanges are inserted through said wedge-receiving slots.

18. The assembly of claim 16, wherein said chemical chamber is removably connected to said flow chamber.

19. The assembly of claim 16, wherein said dispensing control conduit is removably connected to said flow chamber.

* * * * *